(12) United States Patent
Ho

(10) Patent No.: US 6,350,419 B1
(45) Date of Patent: Feb. 26, 2002

(54) COMBINED SUPPORTED LIQUID MEMBRANE/STRIP DISPERSION PROCESS FOR THE REMOVAL AND RECOVERY OF METALS

(75) Inventor: W. S. Winston Ho, Lexington, KY (US)

(73) Assignee: Commodore Separation Technologies Inc., New York, NY (US)

(*) Notice: Subject to any disclaimer, the term of this patent is extended or adjusted under 35 U.S.C. 154(b) by 0 days.

(21) Appl. No.: 09/499,065

(22) Filed: Feb. 4, 2000

(51) Int. Cl.$^7$ .................... C22B 59/00; C22B 15/00; C22B 13/00; C22B 43/00; C22B 17/00
(52) U.S. Cl. .................... 423/21.5; 423/24; 423/89; 423/99; 423/139; 423/510
(58) Field of Search .................... 423/21.5, 24, 139, 423/99, 89, 510; 75/711; 210/638, 643

(56) References Cited

U.S. PATENT DOCUMENTS 4,617,125 A * 10/1986 Danesi .................... 210/638
5,114,579 A * 5/1992 Takigawa .................... 210/638
6,171,563 B1 * 1/2001 Ho .................... 423/54

OTHER PUBLICATIONS

Amanatidou et al., "Method of Cobalt Ion Concentration from Dilute Aqueous Solutions," *Sep. Sci. Technol.;*, 31, 655–664 (1996), No month.
Aouad et al., "Lasalocid (X537 A) as a Selective Carrier for Cd(II) in Supported Liquid Membranes," *J. Membrane Sci.*, 139, 167–174 (1998), No month.
Campderros et al., "Selective Separation of Copper with LIX 864 in a Hollow Fiber Module," *Talanta*, 47, 19–24 (1998), No month.
Daoud et al., "Permeation of Cd(II) Ions through a Supported Liquid Membrane Containing Cyanex–302 in Kerosene," *Sep. Sci. Technol.*, 33, 537–549 (1998), No month.
Dreher and G. W. Stevens, "Instability Mechanism of Supported Liquid Membranes," *Sep. Sci. Technol.*, 33, 835–853 (1998), No month.
El–Reefy et al., "Europium Permeation and Separation from Americium Using Liquid Emulsion Membrane," *Anal. Sci.*, 11, 329–331 (1995), Apr.
Ho and Kamalesh K. Sirkar, eds., Membrane Handbook, Chapman & Hall, New York, 1992, No month.
Hu and J. M. Wiencek, "Emulsion–Liquid–Membrane Extraction of Copper Using a Hollow–Fiber Contractor," *AIChEJ.*, 570–581 (1998), Mar.
Juang and J. D. Jiang, "Rate–Controlling Mechanism of Cobalt Transport through Supported Liquid Membranes Containing Di(2–ethylhexyl) Phosphoric Acid," *Sep. Sci. Technol.*, 29, 223–237 (1994), No month.

(List continued on next page.)

Primary Examiner—Steven Bos
(74) Attorney, Agent, or Firm—Kilpatrick Stockton LLP

(57) ABSTRACT

The present invention provides a novel process for the removal and recovery of metals from waste waters and process streams. The process of the present invention utilizes a combination of a supported liquid membrane (SLM) and a strip dispersion to improve extraction of the target species while increasing membrane stability and reducing processing costs. The process is illustrated with cobalt removal and recovery with unexpected results, such as unexpectedly high cobalt fluxes and a very high cobalt concentration in the strip solution recovered. This process can remove other metals, such as copper, zinc, nickel, mercury, lead, cadmium, silver, europium, lanthanum, neodymium, praseodymium, gadolinium, and selenium, from the feed stream to provide a concentrated strip solution of the target species.

16 Claims, 2 Drawing Sheets

OTHER PUBLICATIONS

Juang and J. D. Jiang, "Recovery of Nickel from a Simulated Electroplating Rinse Solution by Solvent Extraction and Liquid Surfactant Membrane," *J. Membrane Sci.*, 100, 163–170 (1995), No month.

Juang and S. H. Lee, "Analysis of the Transport Rates of Europium(III) across an Organophosphinic Acid Supported Liquid Membrane," *J. Membrane Sci.*, 110, 13–23 (1996), No month.

Kakoi et al., "Separation of Cobalt and Nickel with Phenylposphonic Acid Mono–4–tert–octylphenyl Ester by Liquid Surfactant Membranes," *Sep. Sci. Technol.*, 30, 637–657 (1995), No month.

Kasaini et al., "Application of Emulsion Liquid Membranes to Recover Cobalt Ions from a Dual–component Sulphate Solution Containing Nickel Ions" *J. Membrane Sci.*, 146, 159–168 (1998), No month.

Kunungo and R. Mohapatra, "Coupled Transport of Zn(II) through a Supported Liquid Membrane Containing bis(2,4, 4–Trimethylpentyl) Phosphinic Acid in Kerosene. II Experimental Evaluation of Model Equations for Rate Process under Different Limiting Conditions," *J. Membrane Sci.*, 105, 227–235 (1995), No month.

Lee et al., "Extraction of Trivalent Europium via Emulsion Liquid Membrane Containing PC–88A as Mobile Carrier," *Ind. Eng. Chem. Res.*, 33, 1556–1564 (1994), No month.

Lee et al., "Selective and Simultaneous Extractions of Zn and Cu Ions by Hollow Fiber SLM Modules Containing HEH(EHP) and LIX84," *Sep. Sci. Technol.*, 34, 1689–1701 (1999), No month.

Li et al., "Separation Study of Cadmium through an Emulsion Liquid Membrane Using Triisooctylamine as Mobile Carrier" *Talanta*, 46, 927–932 (1998), No month.

Li et al., "Separation Study of Mercury through an Emulsion Liquid Membrane," *Talanta*, 43, 1837–1842 1996, No month.

J. Vander Linden and R. F. De Ketelaere, "Selective Recuperation of Copper by Supported Liquid Membrane (SLM) Extraction," *J. Membrane Sci.*, 139, 125–135 (1998), No month.

Nakayama et al., "Separation of Rare Earth Metals Using a Supported Liquid Membrane with DTPA," *J. Alloys Compounds*, 225, 288–290 (1995), No month.

Oleinikova et al., "Selective Transport of Zinc through Activated Composite Membranes Containing Di(2–ethylhexyl) Dithiophosphoric Acid as a Carrier," *Polyhedron*, 18, 3353–3359 (1999), No month.

Raghuraman et al., "Emulsion Liquid Membranes for Wastewater Treatment. Equilibrium Models for Some Typical Metal–Extractant Systems," *Environ. Sci. Technol.*, 28, 1090–1098 (1994), No month.

Raghuraman et al., "Emulsion Liquid Membranes for Wastewater Treatment: Equilibrium Models for Lead–and Cadmium–di–2–ethylhexyl Phosphoric Acid Systems," *Environ. Sci. Technol.*, 29, 979–984 (1995), No month.

Reis and J.M.R. Carvalho, "Recovery of Heavy Metals by a Combination of Two Processes: Cementation and Liquid Membrane Permeation," *Minerals Eng.*, 7, 1301–1311 (1994), Oct.

Rovira and A. M. Sastre, "Modelling of Mass Transfer in Facilitated Supported Liquid–Membrane Transport of Palladium(II) Using Di–(2–ethylhexyl) Thiophosphoric Acid," *J. Membrane Sci.*, 149, 241–250 (1998), No month.

Saito, "Selective Transport of Copper(I, II), Cadmium(II), and Zinc(II) Ions through a Supported Liquid Membrane Containing Bathocuproine, Neocuproine, or Bathophenanthroline," *Sep. Sci. Technol.*, 29, 1335–1346 (1994), No month.

Samar et al., "Purification of Waste Waters Containing Heavy Metals by Surfactant Liquid Membrane Extraction," in *Hydrometall. '94, Pap. Int. Symp.*, Chapman & Hall, London, UK, 1994, pp. 635–654, No month.

Strzelbicki and W. Charewicz, "The Liquid Surfactant Membrane Separation of Copper, Cobalt and Nickel from Multicomponent Aqueous Solutions," *Hydrometallurgy*, 5, 243–254 (1980), No month.

Teramoto et al., "Extraction of Lanthanoids by Liquid Surfactant Membranes," *Sep. Sci. Technol.*, 21, 229–250 (1986), No month.

Teramoto et al., "Effect of Recycling of Feed Solution on the Efficiency of Supported Liquid Membrane Module," *Sep. Sci. Technol.*, 29, 1749–1755 (1994), No month.

Valenzuela et al., "Application of Hollow–Fiber Supported Liquid Membranes Technique to the Selective Recovery of a Low Content of Copper from a Chilean Mine Water," *J. Membrane Sci.*, 155. 163–168 (1999), No month.

Yaftian et al., "Rare–earth Metal–ion Separation Using a Supported Liquid Membrane Mediated by a Narrow Rim Phosphorylated Calix[4]arene," *J. Membrane Sci.*, 144, 57–64 (1998), No month.

Zha et al., "Liquid Membrane Processes for Gallium Recovery from Alkaline Solutions," *Ind. Eng. Chem. Res.*, 34, 1799–1809 (1995), No month.

* cited by examiner

COMBINED SUPPORTED LIQUID MEMBRANE/STRIP DISPERSION PROCESS FOR THE REMOVAL AND RECOVERY OF METALS

FIELD OF THE INVENTION

The present invention relates to the removal and recovery of target species, such as metals, from feed solutions, such as waste waters and process streams, using supported liquid membrane technology.

BACKGROUND OF THE INVENTION

Liquid membranes combine extraction and stripping, which are normally carried out in two separate steps in conventional processes such as solvent extractions, into one step. A one-step liquid membrane process provides the maximum driving force for the separation of a targeted species, leading to the best clean-up and recovery of the species (W. S. Winston Ho and Kamalesh K. Sirkar, eds., *Membrane Handbook*, Chapman & Hall, New York, 1992).

There are two types of liquid membranes: (1) supported liquid membranes (SLMs) and (2) emulsion liquid membranes (ELMs). In SLMs, the liquid membrane phase is the organic liquid imbedded in pores of a microporous support, e.g., microporous polypropylene hollow fibers (W. S. Winston Ho and Kamalesh K. Sirkar, eds., *Membrane Handbook*, Chapman & Hall, New York, 1992). When the organic liquid contacts the microporous support, it readily wets the pores of the support, and the SLM is formed.

For the extraction of a target species from a feed solution, the organic-based SLM is placed between two aqueous solutions—the feed solution and the strip solution—where the SLM acts as a semi-permeable membrane for the transport of the target species from the feed solution to the strip solution. The organic liquid in the SLM is immiscible in the aqueous feed and strip streams and contains an extractant, a diluent which is generally an inert organic solvent, and sometimes a modifier.

The use of SLMs to remove metals from aqueous feed solutions has been long pursued in the scientific and industrial community. The removal of metals, including cobalt, copper, nickel, zinc, cadmium, and gallium, from aqueous solutions has been studied (R. S. Juang and J. D. Jiang, "Rate-controlling Mechanism of Cobalt Transport through Supported Liquid Membranes Containing Di(2-ethylhexyl) Phosphoric Acid," *Sep. Sci. Technol.*, 29, 223–237 (1994); T. Saito, "Selective Transport of Copper(I, II), Cadmium(II), and Zinc(II) Ions through a Supported Liquid Membrane Containing Bathocuproine, Neocuproine, or Bathophenanthroline," *Sep. Sci. Technol.*, 29, 1335–1346 (1994); M. Teramoto, N. Ohnishi, and H. Matsuyama, "Effect of Recycling of Feed Solution on the Efficiency of Supported Liquid Membrane Module," *Sep. Sci. Technol.*, 29, 1749–1755 (1994); F. F. Zha, A. G. Fane, and C. J. D. Fell, "Liquid Membrane Processes for Gallium Recovery from Alkaline Solutions," *Ind. Eng. Chem. Res.*, 34, 1799–1809 (1995); S. B. Kunungo and R. Mohapatra, "Coupled Transport of Zn(II) through a Supported Liquid Membrane Containing bis(2,4,4-Trimethylpentyl) Phosphinic Acid in Kerosene. II Experimental Evaluation of Model Equations for Rate Process under Different Limiting Conditions," *J. Membrane Sci.*, 105, 227–235 (1995)).

The extraction of rare earth metals, including europium, lanthanum, and neodymium, with SLMs has been investigated (C. Nakayama, S. Uemiya, and T. Kojima, "Separation of Rare Earth Metals Using a Supported Liquid Membrane with DTPA," *J. Alloys Compounds*, 225, 288–290 (1995); R. S. Juang and S. H. Lee, "Analysis of the Transport Rates of Europium(III) across an Organophosphinic Acid Supported Liquid Membrane," *J. Membrane Sci.*, 110, 13–23 (1996)).

Recently, the removal of metals, including copper, zinc, cadmium, and palladium, with SLMs has been described (N. Aouad, G. Miquel-Mercier, E. Bienvenüe, E. Tronel-Peyroz, G. Jeminet, J. Juillard, and P. Seta, "Lasalocid (X537A) as a Selective Carrier for Cd(II) in Supported Liquid Membranes," *J. Membrane Sci.*, 139, 167–174 (1998); J. A. Daoud, S. A. El-Reefy, and H. F. Aly, "Permeation of Cd(II) Ions through a Supported Liquid Membrane Containing Cyanex-302 in Kerosene," *Sep. Sci. Technol.*, 33, 537–549 (1998); J. Vander Linden and R. F. De Ketelaere, "Selective Recuperation of Copper by Supported Liquid Membrane (SLM) Extraction," *J. Membrane Sci.*, 139, 125–135 (1998); M. E. Campderrós, A. Acosta, and J. Marchese, "Selective Separation of Copper with LIX 864 in a Hollow Fiber Module," *Talanta*, 47, 19–24 (1998); M. Rovira and A. M. Sastre, "Modelling of Mass Transfer in Facilitated Supported Liquid-Membrane Transport of Palladium(II) Using Di-(2-ethylhexyl)Thiophosphoric Acid," *J. Membrane Sci.*, 149, 241–250 (1998); J. C. Lee, J. Jeong, J. T. Park, I. J. Youn, and H. S. Chung, "Selective and Simultaneous Extractions of Zn and Cu Ions by Hollow Fiber SLM Modules Containing HEH(EHP) and LIX84," *Sep. Sci. Technol.*, 34, 1689–1701 (1999); F. Valenzuela, C. Basualto, C. Tapia, and J. Sapag, "Application of Hollow-Fiber Supported Liquid Membranes Technique to the Selective Recovery of a Low Content of Copper from a Chilean Mine Water," *J. Membrane Sci.*, 155, 163–168 (1999); M. Oleinikova, C. González, M. Valiente, and M. Muñoz, "Selective Transport of Zinc through Activated Composite Membranes Containing Di(2-ethylhexyl)Dithiophosphoric Acid as a Carrier," *Polyhedron*, 18, 3353–3359 (1999)).

The extraction of rare earth metals, including europium, lanthanum, neodymium, praseodymium, and gadolinium, with SLMs has been reported recently (M. R. Yaftian, M. Burgard, C. B. Dieleman and D. Matt, "Rare-earth Metal-ion Separation Using a Supported Liquid Membrane Mediated by a Narrow Rim Phosphorylated Calix[4]arene," *J. Membrane Sci.*, 144, 57–64 (1998)).

One disadvantage of SLMs is their instability due mainly to loss of the membrane liquid (organic solvent, extractant, and/or modifier) into the aqueous phases on each side of the membrane (A. J. B. Kemperman, D. Bargeman, Th. Van Den Boomgaard, H. Strathmann, "Stability of Supported Liquid Membranes: State of the Art," *Sep. Sci. Technol.*, 31, 2733 (1996); T. M. Dreher and G. W Stevens, "Instability Mechanisms of Supported Liquid Membranes," *Sep. Sci. Technol.*, 33, 835–853 (1998); J. F. Dozol, J. Casas, and A. Sastre, "Stability of Flat Sheet Supported Liquid Membranes in the Transport of Radionuclides from Reprocessing Concentrate Solutions," *J. Membrane Sci.*, 82, 237–246 (1993)). The prior art has attempted to solve this problem through the combined use of SLM with a module containing two sets of hollow fibers, i.e., the hollow-fiber contained liquid membrane (W. S. Winston Ho and Kamalesh K. Sirkar, eds., *Membrane Handbook*, Chapman & Hall, New York, 1992). In this configuration, with two sets of microporous hollow-fiber membranes, one set of membranes carries the aqueous feed solution, and the other carries the aqueous strip solution. The organic phase is contained between the two sets of hollow fibers by maintaining the aqueous phases at a higher pressure than the organic phase. The use of the hollow-fiber contained liquid membrane increases membrane stability because the liquid membrane may be continuously replenished. However, this configuration is not advantageous because it requires mixing two sets of fibers to achieve a low contained liquid membrane thickness.

In ELMs, an emulsion acts as a liquid membrane for the separation of the target species from a feed solution. An ELM is created by forming a stable emulsion, such as a water-in-oil emulsion, between two immiscible phases, followed by dispersion of the emulsion into a third, continuous phase by agitation for extraction. The membrane phase is the oil phase that separates the encapsulated, internal aqueous droplets in the emulsion from the external, continuous phase (W. S. Winston Ho and Kamalesh K. Sirkar, eds., *Membrane Handbook*, Chapman & Hall, New York, 1992). The species-extracting agent is contained in the membrane phase, and the stripping agent is contained in the internal aqueous droplets. Emulsions formed from these two phases are generally stabilized by use of a surfactant. The external, continuous phase is the feed solution containing the target species. The target species is extracted from the aqueous feed solution into the membrane phase and then stripped into the aqueous droplets in the emulsion. The target species can then be recovered from the internal, aqueous phase by breaking the emulsion, typically via electrostatic coalescence, followed by electroplating or precipitation.

The use of ELMs to remove metals from aqueous feed solutions has also been long pursued in the scientific and industrial community. ELMs for the removal of metals, including cobalt, copper, zinc, nickel, mercury, lead, cadmium, silver, europium, lanthanum, and neodymium, have been described in detail (W. S. Winston Ho and Kamalesh K. Sirkar, eds., *Membrane Handbook*, Chapman & Hall, New York, 1992). The removal of cobalt, copper, and nickel from aqueous solutions by ELMs has also been investigated (J. Strzelbicki and W. Charewicz, "The Liquid Surfactant Membrane Separation of Copper, Cobalt and Nickel from Multicomponent Aqueous Solutions," *Hydrometallurgy*, 5, 243–254 (1980)). The extraction of lanthanoids, including europium, lanthanum, neodymium, and gadolinium, with ELMs has been studied (M. Teramoto, T. Sakuramoto, T. Koyama, H. Matsuyama, and Y. Miyake, "Extraction of Lanthanoids by Liquid Surfactant Membranes," *Sep. Sci. Technol.*, 21, 229–250 (1986); C. J. Lee, S. S. Wang, and S. G. Wang, "Extraction of Trivalent Europium via Emulsion Liquid Membrane Containing PC-88A as Mobile Carrier, *Ind. Eng. Chem. Res.*, 33, 1556–1564 (1994); S. A. El-Reefy, M. R. El-Sourougy, E. A. El-Sherif, and H. F. Aly, "Europium Permeation and Separation from Americium Using Liquid Emulsion Membrane," *Anal. Sci.*, 11, 329–331 (1995)).

Recently, the removal of metals including cobalt, nickel, cadmium, mercury, and lead with ELMs has been reported (M. Samar, D. Pareau, G. Durand, and A. Chesne, "Purification of Waste Waters Containing Heavy Metals by Surfactant Liquid Membrane Extraction," in *Hydrometall. '94, Pap. Int. Symp.*, Chapman & Hall, London, UK, 1994, pp. 635–654; B. Raghuraman, N. Tirmizi, and J. M. Wiencek, "Emulsion Liquid Membranes for Wastewater Treatment. Equilibrium Models for Some Typical Metal-Extractant Systems," *Environ. Sci. Technol.*, 28, 1090–1098 (1994); M. T. A. Reis and J. M. R. Carvalho, "Recovery of Heavy Metals by a Combination of Two Processes: Cementation and Liquid Membrane Permeation," *Minerals Eng.*, 7, 1301–1311 (1994); T. Kakkoi, M. Goto, K. Sugimoto, K. Ohto, and F. Nakashio, "Separation of Cobalt and Nickel with Phenylphosphonic Acid Mono-4-tert-octylphenyl Ester by Liquid Surfactant Membranes," *Sep. Sci. Technol.*, 30, 637–657 (1995); R. S. Juang and J. D. Jiang, "Recovery of Nickel from a Simulated Electroplating Rinse Solution by Solvent Extraction and Liquid Surfactant Membrane," *J. Membrane Sci.*, 100, 163–170 (1995); B. J. Raghuraman, N. P. Tirmizi, B. S. Kim, and J. M. Wiencek, "Emulsion Liquid Membranes for Wastewater Treatment: Equilibrium Models for Lead- and Cadmium-di-2-ethylhexyl Phosphoric Acid Systems," *Environ. Sci. Technol.*, 29, 979–984 (1995); E. Amanatidou, M. N. Stefanut, and A. Grozav, "Method of Cobalt Ion Concentration from Dilute Aqueous Solutions," *Sep. Sci. Technol.*, 31, 655–664 (1996); Q. Li, Q. Liu, and X. Wei, "Separation Study of Mercury through an Emulsion Liquid Membrane," *Talanta*, 43, 1837–1842 (1997); H. Kasaini, F. Nakashio, and M. Goto, "Application of Emulsion Liquid Membranes to Recover Cobalt Ions from a Dual-component Sulphate Solution Containing Nickel Ions," *J. Membrane Sci.*, 146, 159–168 (1998); Q. M. Li, Q. Liu, Q. F. Zhang, X. J. Wei, and J. Z. Guo, "Separation Study of Cadmium through an Emulsion Liquid Membrane Using Triisooctylamine as Mobile Carrier," *Talanta*, 46, 927–932 (1998); S. Y. B. Hu and J. M. Wiencek, "Emulsion-Liquid-Membrane Extraction of Copper Using a Hollow-Fiber Contactor," *AIChE J.*, 570–581 (1998)).

One disadvantage of ELMs is that the emulsion swells upon prolonged contact with the feed stream. This swelling causes a reduction in the stripping reagent concentration in the aqueous droplets which reduces stripping efficiency. It also results in dilution of the target species that has been concentrated in the aqueous droplets, resulting in lower separation efficiency of the membrane. The swelling further results in a reduction in membrane stability by making the membrane thinner. Finally, swelling of the emulsion increases the viscosity of the spent emulsion, making it more difficult to demulsify. A second disadvantage of ELMs is membrane rupture, resulting in leakage of the contents of the aqueous droplets into the feed stream and a concomitant reduction of separation efficiency. Raghuraman and Wiencek (B. Raghuraman and J. Wiencek, "Extraction with Emulsion Liquid Membranes in a Hollow-Fiber Contactor," *AIChE J.*, 39, 1885–1889 (1993)) have described the use of microporous hollow-fiber contactors as an alternative contacting method to direct dispersion of ELMs to minimize the membrane swelling and leakage. The hollow-fiber contactors minimize membrane swelling and leakage because they do not have the high shear rates typically encountered with the agitators used in the direct dispersion. Additional disadvantages of ELMs include the necessary process steps for making and breaking the emulsion.

Thus, there is a need in the art for an extraction process which maximizes the stability of the SLM membrane, resulting in efficient removal and recovery of metals from the aqueous feed solutions.

SUMMARY OF THE INVENTION

The present invention relates generally to a process for the removal and recovery of target species from a feed solution using a combined SLM/strip dispersion. In one embodiment, the present invention relates to a process for the removal and recovery of a metal or metals from a feed solution which comprises the following steps. First, a feed solution containing one or more metals is passed on one side of the SLM embedded in a microporous support material and treated to remove the metal or metals by the use of a strip dispersion on the other side of the SLM. the strip dispersion can be formed by dispersing an aqueous strip solution in an organic liquid, for example, using a mixer. Second, the strip dispersion, or a part of the strip dispersion is allowed to stand, resulting in separation of the dispersion into two phases: the organic liquid phase and the aqueous strip solution phase containing a concentrated metal solution.

The continuous organic phase of the strip dispersion readily wets the pores of a microporous support to form a stable SLM. The process of the present invention provides a number of operational and economic advantages over the use of conventional SLMs.

Thus, it is an object of the present invention to provide an SLM process for the removal and recovery of target species which provides increased membrane stability.

It is another object of the present invention to provide an SLM process for the removal and recovery of one or more metals from a feed solution.

It is yet another object of the present invention to provide a process for the removal and recovery of cobalt, copper, zinc, nickel, mercury, lead, cadmium, silver, europium, lanthanum, neodymium, praseodymium, gadolinium, and selenium from a feed solution.

It is an object of the present invention to provide an SLM process having improved flux.

It is another object of the present invention to provide an SLM process having improved recovery of the target species to provide a concentrated strip solution.

It is a further object of the invention to provide an SLM process for the removal and recovery of a target species from a feed solution which exhibits decreased operation costs and a decreased capital investment over convention SLM processes.

It is an object of the invention to provide a process for the removal and recovery of target species from a feed solution using a combined SLM/strip dispersion method.

DESCRIPTION OF THE PREFERRED EMBODIMENTS

The present invention relates to a process for the removal and recovery of a target species from a feed solution, such as waste waters or process streams. In one embodiment of the present invention, the target species is a metal. Preferred metal species include, but are not limited to, cobalt, copper, zinc, nickel, mercury, lead, cadmium, silver, europium, lanthanum, neodymium, praseodymium, gadolinium, and selenium. This new process employs a combination of a supported liquid membrane (SLM) and a strip dispersion.

The process of the invention comprises the following steps. First, a feed solution containing one or more metals is passed on one side of the SLM embedded in a microporous support material and treated to remove the metal or metals by the use of a strip dispersion on the other side of the SLM. the strip dispersion can be formed by dispersing an aqueous strip solution in an organic liquid, for example, using a mixer. Second, the strip dispersion, or a part of the strip dispersion is allowed to stand, resulting in separation of the dispersion into two phases: the organic liquid phase and the aqueous strip solution phase containing a concentrated metal solution.

Figure 1:
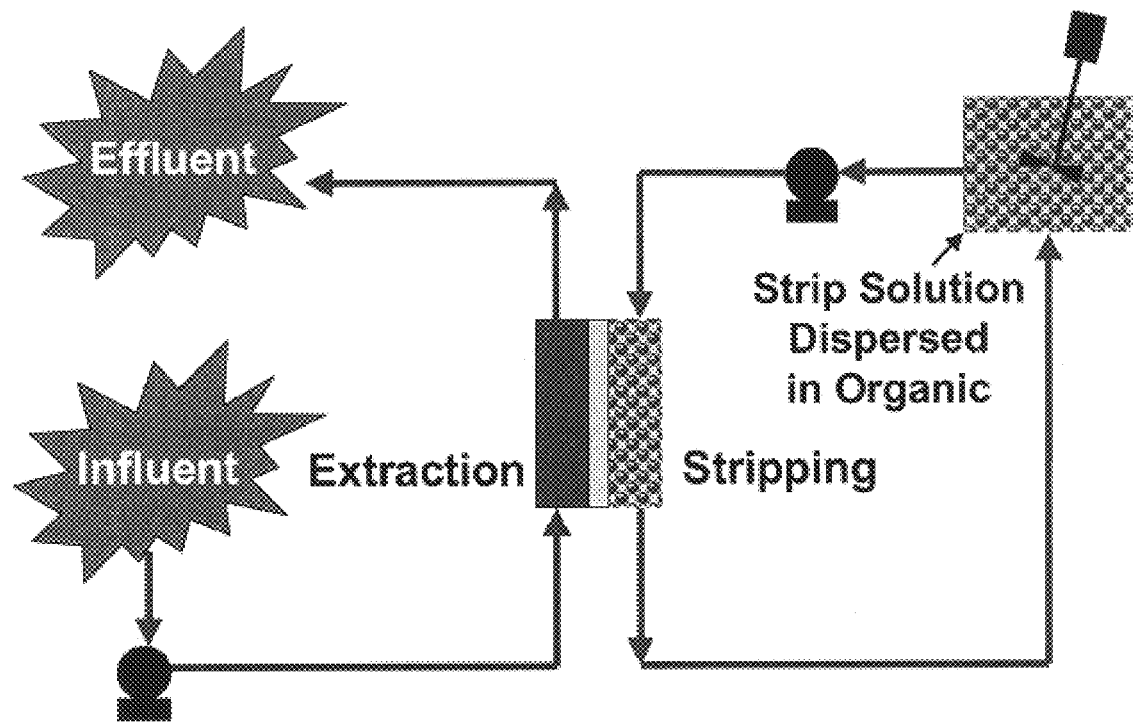
FIG. 1 is a schematic representation of the combined supported liquid membrane/strip dispersion of the present invention.

While any SLM configuration may be employed in the process of the invention, the preferred configuration employs a hollow fiber module as the liquid membrane microporous support. Such hollow fiber modules consist of microporous hollow fibers arranged in a shell-and-tube configuration. In the present invention, the strip dispersion is passed through either the shell side of the module or the tube side of the module, and the aqueous feed solution containing the target species for extraction is passed through the opposing side of the module. The use of the hollow fiber system in the combined SLM/strip dispersion process allows continuous replenishment of the strip dispersion as shown in FIG. 1, ensuring a stable and continuous operation.

For the purposes of the invention, strip dispersion is defined as a mixture of an aqueous phase and an organic phase. The aqueous phase of the dispersion comprises an aqueous strip solution, while the organic phase comprises an extractant or extractants in an organic liquid. The dispersion is formed by the mixing of the aqueous and organic phases as shown in FIG. 1. This combination results in droplets of the aqueous strip solution in a continuous organic phase. The dispersion is maintained during the extraction process due to the flow of the dispersion through a membrane module, e.g., a hollow fiber module. The continuous organic phase of the strip dispersion readily wets the hydrophobic pores of the microporous hollow fibers in the module, forming a stable liquid membrane.

Figure 2:
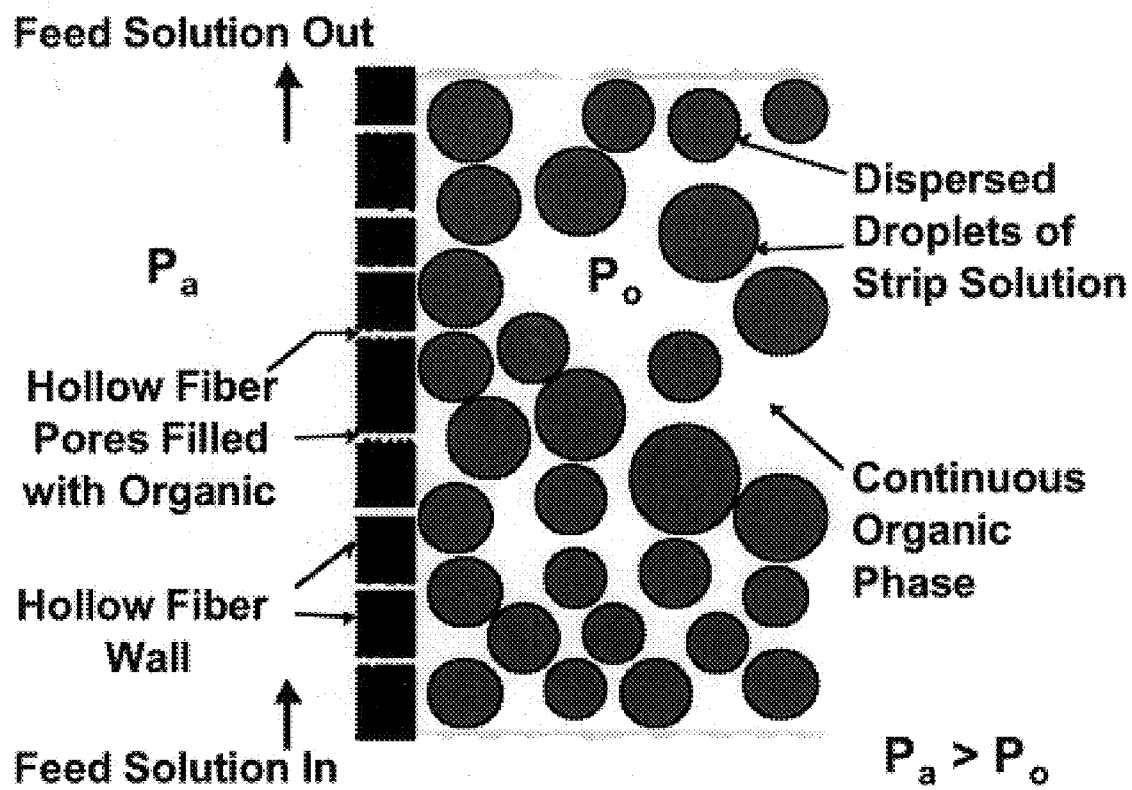
FIG. 2 is an enlarged view of the schematic representation of the combined supported liquid membrane/strip dispersion of the present invention.

FIG. 2 shows an enlarged view of a schematic representation of the SLM with strip dispersion of the present invention. A low pressure, $P_a$, which is typically less than approximately 2 psi, is applied on the feed solution side of the SLM. The pressure $P_a$ is greater than the pressure, $P_o$, on the strip dispersion side of the SLM. This difference in pressure prevents the organic solution of the strip dispersion from passing through the pores to come into the feed solution side. The dispersed droplets of the aqueous strip solution have a typical size of about 80 to about 800 micrometers and are orders of magnitude larger than the pore size of the microporous support employed for the SLM, which is in the order of approximately 0.03 micrometer. Thus, these droplets are retained on the strip dispersion side of the SLM and cannot pass through the pores to go to the feed solution side.

In this SLM/strip dispersion system, there is a constant supply of the organic membrane solution, i.e. the organic phase of the strip dispersion, into the pores. This constant supply of the organic phase ensures a stable and continuous operation of the SLM. In addition, the direct contact between the organic and strip phases provides efficient mass transfer for stripping. The organic and strip phases can be mixed, for example, with high-shear mixing to increase the contact between the two phases.

Once removal of the target species is complete, the mixer for the strip dispersion is stopped, and the dispersion is allowed to stand until it separates into two phases, the organic membrane solution and the concentrated strip solution. The concentrated strip solution is the product of this process.

The feed solution includes, but is not limited to, waste waters or process streams containing metals. The metals include, but are not limited to, cobalt, copper, zinc, nickel, mercury, lead, cadmium, silver, europium, lanthanum, neodymium, praseodymium, gadolinium, and selenium.

The microporous support employed in the invention is comprised of, for example, microporous polypropylene, polytetrafluoroethylene, polyethylene, polysulfone, polyethersulfone, polyetheretherketone, polyimide, polyamide, or mixtures thereof. The preferred microporous support is microporous polypropylene hollow fibers.

The aqueous portion of the strip dispersion comprises an aqueous acid solution, such as a mineral acid. Examples of acids useful in the present invention include, but are not limited to, sulfuric acid ($H_2SO_4$), hydrochloric acid (HCl), nitric acid ($HNO_3$), phosphoric acid ($H_3PO_4$), and acetic acid ($CH_3COOH$). The acid is present in a concentration between about 0.1 M and about 18 M. The preferred concentration for the acid solution is between about 1 M and about 3 M.

The continuous organic liquid phase into which the aqueous strip solution is dispersed contains an extractant or extractants. The extractant is capable of extracting the target species contained in the feed solution. Typical extractants which are known in the art for extraction of species from waste waters or process streams may be employed in the present strip dispersion. Some nonlimiting examples of such extractants include, di(2,4,4-trimethylpentyl) dithiophosphonic acid), a nonylsalicyl aldoxime and ketoxime extractant system 9 e.g., LIX 973N containing about 46% nonylsalicyl aldoxime, 18% ketoxime, 6% nonylphenol, and 30% diluent), di(2-ethylhexyl)phosphoric acid (D2EHPA), and oleic acid. Selection of such extractants based upon the specific target species to be extracted is within the level of skill in the art.

In addition to conventional extractants, any other extractant that will extract the metal species contained in the feed solution can be employed in the present invention. For example, the new extractant, di(2-butyloctyl) monothiophosphoric acid (C12 MTPA), is particularly useful for the removal and recovery of nickel.

The organic liquid of the present strip dispersion optionally comprises a hydrocarbon solvent or mixture. The hydrocarbon solvent or mixture has a number of carbon atoms per solvent molecule ranging from 6 to 18, preferably from 10 to 14. The hydrocarbon solvent includes, for example, n-decane, n-undecane, n-dodecane, n-tridecane, n-tetradecane, isodecane, isoundecane, isododecane, isotridecane, isotetradecane, isoparaffinic hydrocarbon solvent (with a flash point of 92° C., a boiling point of 254° C., a viscosity of 3 cp (at 25° C.), and a density of 0.791 g/ml (at 15.6° C.)) or mixtures thereof.

The organic liquid of the present strip dispersion optionally contains a modifier to enhance the complexation and/or stripping of the target species. The modifier can be, for example, an alcohol, a nitrophenyl alkyl ether, a trialkyl phosphate or mixtures thereof. The alcohol can be, for example, hexanol, heptanol, octanol, nonanol, decanol, undecanol, dodecanol, tridecanol, tetradecanol, pentadecanol, hexadecanol, heptadecanol, octadecanol or mixtures thereof. The nitrophenyl ether can be, for example, o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether or mixtures thereof. The trialkyl phosphate can be, for example, tributyl phosphate, tris(2-ethylhexyl)phosphate or mixtures thereof. The above lists of modifiers are nonlimiting examples of modifiers that can be used in the present invention. Other similar modifiers as will be appreciated by those skilled in the art can also be employed as modifiers in the present invention.

The organic liquid of the present strip dispersion comprises about 2%–100% (approximately 0.05M–3M) extractant and about 0%–20% modifier in a hydrocarbon solvent or mixture. More preferably, the organic liquid of the present strip dispersion comprises about 5%–40% extractant and about 1%–10% modifier in a hydrocarbon solvent or mixture. Even more preferably, the organic liquid comprises about 5%–40% extractant and about 1%–10% dodecanol in an isoparaffinic hydrocarbon solvent or in n-dodecane. All percentages are by weight unless specified otherwise.

The present invention has several advantages over conventional SLM technology. These advantages include increased membrane stability, reduced costs, increased simplicity of operation, improved flux, and improved recovery of target species concentration.

The present invention provides a constant supply of the organic membrane solution into the pores of the hollow fiber support. This constant supply results in an SLM which is more stable than conventional SLMs, ensuring stable and continuous operation. This constant supply also eliminates the need for recharging membrane modules, which is required with conventional SLMs. It further eliminates the need for a second set of membrane modules for use during recharging of the first set of membrane modules. Thus, the present invention decreases not only operational costs but also the initial capital investment in the system. The present invention also increases simplicity of the removal operation.

The present invention provides direct contact between the organic/extraction phase and aqueous strip phase. Mixing of these phases provides an extra mass transfer surface area in addition to the area given by the hollow fibers, leading to extremely efficient stripping of the target species from the organic phase. This efficient stripping enhances the flux for the extraction of many targeted species. For example, fluxes of about 3 $g/(m^2*hr)$ or higher for treatment of the feed solution are typical for the present invention. In fact, unexpectedly high flux results with the present invention as compared to those observed with conventional SLM separation processes. Particularly advantageous fluxes result with the present process when it is used for the removal and recovery of cobalt.

The present invention comprises a new type of SLM which provides increased flexibility of aqueous strip/organic volume ratio. This flexibility allows the use of a smaller volume of aqueous strip solution to obtain a higher concentration of the recovered target species in the aqueous strip solution. The concentrated strip solution is a valuable product for resale or reuse.

This invention is further illustrated by the following examples, which are not to be construed in any way as imposing limitations upon the scope thereof. To the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

GENERAL PROCEDURE

The strip dispersion for each of the following examples was prepared by mixing an aqueous strip solution in a quantity of, for example, 200 ml, and an organic extractant solution (for example, dodecane containing 2 wt. % dodecanol and 8 wt. % extractant) in a quantity of, for example, 600 ml, in a Fisher brand mixer with a 2-inch diameter, 6-bladed, high-shear impeller at 500 rpm as measured by an Ono Sokki HT-4100 tachometer. The mixer was plugged into a varistat to allow for adjustable speed control. The impeller was initially started at 50% of its full power and the varistat at 80%.

All of the following examples were run in countercurrent fashion with the feed solution passed through the tube side of the microporous polypropylene hollow fiber module. The hollow-fiber moldule was 2.5 inches in diameter and 8 inches in length, providing a surface area of 1.4 m². The process was first started by passing water through the hollow fiber module. The pressures were adjusted to provide a positive pressure on the feed side of the hollow fiber module. Once the pressures were adjusted and stable, the water was replaced with the feed solution. A positive pressure was maintained on the feed side to prevent the organic phase in the shell side from passing through the pores of the hollow fibers.

The pressure of the inlet on the shell side was maintained at 1.25 psi and the outlet pressure of the feed side was set at 3.25 psi, thus maintaining a 2 psi differential between the two sides. In each of the runs, the feed flow was adjusted to give a flow rate of approximately 0.84 liter/min at these pressures. The typical feed solution volume for these experiments was 4 liters.

Samples from the feed solution and the strip dispersion were taken at timed intervals. The strip dispersion samples were allowed to stand until phase separation occurred. The aqueous phase from the strip dispersion sample was then collected and centrifuged to facilitate complete separation. The aqueous phase samples from the strip dispersion samples and the feed solution samples were then analyzed by inductively coupled plasma (ICP) spectrometry.

The flux of a species removed from the feed solution can be defined by the following formula:

$$\text{flux} = \frac{V \Delta C}{tA}$$

where V is the volume of the feed solution treated; $\Delta C$ is the concentration change in the feed solution; t is the time at which the sample was taken; and A is the membrane surface area. The flux of the species was calculated from the above equation.

The mass transfer coefficient k of the species removed from the feed solution can be defined by the following formula:

$$k = \frac{V}{tA} \ln\left(\frac{C_o}{C_t}\right)$$

where $C_o$ is the initial concentration of the species in the feed solution; $C_t$ is the concentration of the species in the feed solution at time t; t is the time; and the rest of the symbols are as defined above. The mass transfer coefficient k of the species was calculated from the above equation.

Example 1
Unexpectedly High Flus Results for Cobalt

A fresh solution of 2.5 M $H_2SO_4$ was prepared for use as the strip solution. A strip dispersion was then prepared by mixing together 200 ml of the 2.5 M $H_2SO_4$ solution and 600 ml of an organic solution containing 24 wt. % di(2,4,4-trimethylpentyl)dithiophosphinic acid (e.g., Cyanex 301), 2 wt. % dodecanol, and 74 wt. % Isopar L as described in the general procedure above. This strip dispersion was then fed into the shell side of a 2.5-inch diameter polypropylene hollow fiber module (2.5 inches in diameter by 8 inches in length). A feed solution containing a cobalt concentration of 489 parts per million (ppm) was passed into the tube side of the hollow fiber module. The pH of the feed solution was maintained at 2.3±0.1 by adding 5 M NaOH as needed. Samples of the feed and strip solutions were collected at timed intervals and analyzed by ICP as described in the general procedure above. Fluxes and k values were then calculated and are reported in Table 1 below.

The cobalt was removed from the feed solution, concentrated, and recovered in the aqueous strip solution. The cobalt flux of 8.777 g/(m²*hr) at a cobalt concentration of 233 ppm in the feed solution was unexpectedly high in comparison with the cobalt flux obtained under similar conditions with the conventional SLM as described in Example 3. The fluxes for the latter, even at the higher cobalt concentrations of 358 ppm and 272 ppm in the feed solution, were only 1.954 and 1.474 g/(m²*hr), respectively. Thus, cobalt flux with the present invention was more than 4.5 times higher than that with conventional SLM.

In addition, the extractant concentration of 24 wt. % was much lower than the extractant concentration for the conventional SLM in Example 3 which was about 37 wt. %. In general, a higher extractant concentration should give a higher flux. Thus, the high flux of the seen with the present invention was an unexpected result.

TABLE 1

| Co Results | | Cyanex 301 | Strip Dispersion | | 2.5M $H_2SO_4$ |
|---|---|---|---|---|---|
| Time (min.) | pH | Strip (ppm) | Feed (ppm) | Feed Flux (g/(m²*hr)) | k value (cm/sec) |
| 0 | 2.3 | | 489 | | |
| 5 | | | 233 | 8.777 | 0.000706 |
| 10 | | 2791 | 108 | 4.286 | 0.000732 |
| 15 | | | 50.3 | 1.978 | 0.000728 |
| 20 | | 4782 | 23.3 | 0.926 | 0.000733 |
| 30 | | 5410 | 4.37 | 0.325 | 0.000797 |

Example 2
Unexpectedly High Flux Results for Cobalt

The experimental procedure for this example was the same as that described in Example 1, except that a feed solution containing 571 ppm cobalt and the used strip dispersion from the preceding example were employed. The excess aqueous strip and organic solutions from the strip dispersion samples from the preceding example were returned to the strip dispersion tank before the start of this experiment. Samples of the feed and strip solutions were collected at timed intervals and analyzed by ICP as described in the general procedure above. Fluxes and k values were then calculated and are reported in Table 2.

The cobalt was removed from the feed solution, concentrated, and recovered in the aqueous strip solution. The cobalt flux of 10.217 g/(m²*hr) at the cobalt concentration of 273 ppm in the feed solution was unexpectedly high in comparison with the cobalt flux obtained under the similar conditions with the conventional SLM described in Example 3. The fluxes for the latter, even at a higher cobalt concentration of 358 ppm and a similar cobalt concentration of 272 ppm in the feed solution, were only 1.954 and 1.474 g/(m²*hr), respectively. Thus, the cobalt flux with the present invention was more than 5.2 times higher than that with the conventional SLM. In addition, the extractant concentration of 24 wt. % was much lower than that of about 37 wt. % for the conventional SLM in Example 3. As mentioned, a higher extractant concentration should generally give a higher flux.

Again, the high flux was an unexpected result of the present invention.

TABLE 2

| Co Results Time (min.) | pH | Cyanex 301 Strip (ppm) | Strip Dispersion Feed (ppm) | Feed Flux (g/(m$^2$*hr)) | 2.5M H$_2$SO$_4$ k value (cm/sec) |
|---|---|---|---|---|---|
| 0 | 2.3 | 5338 | 571 | | |
| 5 | | | 273 | 10.217 | 0.000703 |
| 10 | | 9289 | 131 | 4.869 | 0.000699 |
| 15 | | | 60.3 | 2.424 | 0.000739 |
| 20 | | 10394 | 28.0 | 1.107 | 0.000731 |
| 30 | | 10478 | 6.18 | 0.374 | 0.000719 |

Example 3
Comparative Example Using Conventional SLM

As described in the Background of the Invention, the organic membrane phase of the conventional SLM (imbedded in a microporous support) was placed between two aqueous solutions—the feed solution and a strip solution that was not a strip dispersion. The microporous support used for this example was the same type and the same size of the hollow fiber module employed and described in Example 1. The organic membrane solution was similar to that used in Example 1 except the concentration of the extractant, di(2,4,4-trimethylpentyl)dithiophosphinic acid (e.g., Cyanex 301), was higher, i.e., 1 M (approximately 37 wt. % instead of the 24 wt. % used in Example 1). In a manner similar to Example 1, a feed solution containing 472 ppm cobalt and a sulfuric acid strip solution were used in Example 3. In the same way as in Example 1, the pH of the feed solution was maintained by adding 5 M NaOH as needed. Also in a similar countercurrent flow configuration, the feed solution was passed into the tube side of the hollow fiber module, whereas the strip solution was fed into the shell side of the module. Samples of the feed and strip solutions were collected at timed intervals and analyzed by ICP as described in the general procedure above. Fluxes and k values were then calculated and are reported in Table 3.

As shown in Table 3, the cobalt fluxes at the cobalt concentrations of 358 ppm and 272 ppm in the feed solution were only 1.954 and 1.474 g/(m$^2$*hr), respectively. These fluxes were much lower than those with the present invention described in Examples 1 and 2, in spite of much higher extractant concentrations. In general, a higher extractant concentration should give a higher flux. In other words, there were unexpected results with the present invention.

TABLE 3

| Co Results Time (min.) | pH | Cyanex 301 Strip (ppm) | Conventional SLM Feed (ppm) | Feed Flux (g/(m$^2$*hr)) | 2.5M H$_2$SO$_4$ k value (cm/sec) |
|---|---|---|---|---|---|
| 0 | 2.3 | 0 | 472 | | |
| 5 | | 118 | 358 | 1.954 | 0.000132 |
| 10 | | 250 | 272 | 1.474 | 0.000131 |
| 15 | | 397 | 195 | 1.320 | 0.000159 |
| 20 | | 532 | 115 | 1.371 | 0.000252 |
| 30 | | 742 | 12.8 | 0.876 | 0.000523 |

Example 4
Organic Solution Comprising 8% Extractant and 2% Dodecanol for Cobalt

The experimental procedure for this example was the same as that described in Example 1, except that a feed solution containing 562 ppm cobalt and an organic solution of the strip dispersion containing 8 wt. % di(2,4,4-trimethylpentyl)dithiophosphinic acid (e.g., Cyanex 301), 2 wt. % dodecanol, and 90 wt. % Isopar L were used. Samples of the feed and strip solutions were collected at timed intervals and analyzed by ICP as described in the general procedure above. Fluxes and k values were then calculated and are reported in Table 4.

The cobalt was removed from the feed solution, concentrated, and recovered in the aqueous strip solution. The cobalt flux of 7.406 g/(m$^2$*hr) at a cobalt concentration of 346 ppm in the feed solution was unexpectedly high in comparison with the cobalt flux obtained under the similar conditions with the conventional SLM described in Example 3. The flux for the latter, even at a higher cobalt concentration of 358 ppm in the feed solution, was only 1.954 g/(m$^2$*hr). Thus, the cobalt flux with the present invention was at least 3.8 times higher than that with the conventional SLM. In addition, the extractant concentration of 8 wt. % for the present Example was much lower than that of about 37 wt. % for the conventional SLM in Example 3. As mentioned, a higher extractant concentration should generally give a higher flux. Again, the high flux of the present invention was an unexpected result.

TABLE 4

| Co Results Time (min.) | pH | Cyanex 301 Strip (ppm) | Strip Dispersion Feed (ppm) | Feed Flux (g/(m$^2$*hr)) | 2.5M H$_2$SO$_4$ k value (cm/sec) |
|---|---|---|---|---|---|
| 0 | 2.3 | 1631 | 562 | | |
| 5 | | | 346 | 7.406 | 0.000462 |
| 10 | | 5502 | 184 | 5.554 | 0.000601 |
| 15 | | | 89 | 3.257 | 0.000692 |
| 20 | | 8504 | 43.2 | 1.570 | 0.000688 |
| 30 | | 9233 | 9.76 | 0.573 | 0.000708 |

Example 5
Orgainc Solution Comprising 8% Extractant and 2% Dodecanol for Cobalt

The experimental procedure for this example was the same as that described in Example 4, except that a feed solution containing 567 ppm cobalt and the used strip dispersion from the Example 4 were used. The excess aqueous strip and organic solutions from the strip dispersion samples of Example 4 were returned to the strip dispersion tank before the start of the run for this experiment. Samples of the feed and strip solutions were collected at timed intervals and analyzed by ICP as described in the general procedure above. Fluxes and k values were then calculated and are reported in Table 5.

The cobalt was removed from the feed solution, concentrated, and recovered in the aqueous strip solution. The cobalt flux of 8.023 g/(m$^2$*hr) at a cobalt concentration of 333 ppm in the feed solution was unexpectedly high in comparison with the cobalt flux obtained under the similar conditions with the conventional SLM described in Example 3. The flux for the latter, even at a higher cobalt concentration of 358 ppm in the feed solution, was only 1.954 g/(m$^2$*hr). Thus, the cobalt flux with the present invention was more than 4.1 times higher than that with the conventional SLM. In addition, the extractant concentration of 8 wt. % for the present Example was much lower than that of about 37 wt. % for the conventional SLM in Example 3. As mentioned, a higher extractant concentration should gener ally give a higher flux. Again, the high flux was an unexpected result of the present invention.

TABLE 5

| Co Results Time (min.) | pH | Cyanex 301 Strip (ppm) | Strip Dispersion Feed (ppm) | Feed Flux (g/(m²*hr)) | 2.5M H₂SO₄ k value (cm/sec) |
|---|---|---|---|---|---|
| 0 | 2.3 | 9650 | 567 | | |
| 5 | | | 333 | 8.023 | 0.000507 |
| 10 | | 14091 | 175 | 5.417 | 0.000613 |
| 15 | | | 89.1 | 2.945 | 0.000643 |
| 20 | | 17217 | 43.6 | 1.560 | 0.000681 |
| 30 | | 17627 | 9.83 | 0.579 | 0.000709 |

Example 6
Organic Solution Comprising 8% Extractant and 3% Dodecanol for Cobalt

The experimental procedure for this example was the same as that described in Examples 1 and 4, except that a feed solution containing 562 ppm cobalt and an organic solution of the strip dispersion containing 8 wt. % di(2,4,4-trimethylpentyl)dithiophosphinic acid (e.g., Cyanex 301), 3 wt. % dodecanol, and 89 wt. % Isopar L were used. Samples of the feed and strip solutions were collected at timed intervals and analyzed by ICP as described in the general procedure above. Fluxes and k values were then calculated and are reported in Table 6.

The cobalt was removed from the feed solution, concentrated, and recovered in the aqueous strip solution. The cobalt flux of 6.960 g/(m²*hr) at the cobalt concentration of 359 ppm in the feed solution was unexpectedly high in comparison with the cobalt flux obtained under the similar conditions with the conventional SLM described in Example 3. The flux for the latter at a similar cobalt concentration of 358 ppm in the feed solution was only 1.954 g/(m²*hr). Thus, the cobalt flux with the present invention was more than 3.6 times higher than that with the conventional SLM. In addition, the extractant concentration of 8 wt. % for the present example was much lower than that of about 37 wt. % for the conventional SLM in Example 3. As mentioned, a higher extractant concentration should generally give a higher flux. Again, the high flux was an unexpected result of the present invention.

TABLE 6

| Co Results Time (min.) | pH | Cyanex 301 Strip (ppm) | Strip Dispersion Feed (ppm) | Feed Flux (g/(m²*hr)) | 2.5M H₂SO₄ k value (cm/sec) |
|---|---|---|---|---|---|
| 0 | 2.3 | 2561 | 562 | | |
| 5 | | | 359 | 6.960 | 0.000427 |
| 10 | | 5957 | 197 | 5.554 | 0.000572 |
| 15 | | | 105 | 3.154 | 0.000599 |
| 20 | | 8814 | 52 | 1.817 | 0.000669 |
| 30 | | 10109 | 12.2 | 0.682 | 0.000690 |

Example 7
Organic Solution Comprising 8% Extractant and 3% Dodecanol for Cobalt

The experimental procedure for this example was the same as that described in Example 6, except that a feed solution containing 551 ppm cobalt and the used strip dispersion from Example 6 were employed. The excess aqueous strip and organic solutions from the strip dispersion samples from Example 6 were returned to the strip dispersion tank before the start of this experiment. Samples of the feed and strip solutions were collected at timed intervals and analyzed by ICP as described in the general procedure above. Fluxes and k values were then calculated and are reported in Table 7.

The cobalt was removed from the feed solution, concentrated, and recovered in the aqueous strip solution. The cobalt flux of 6.926 g/(m²*hr) at the cobalt concentration of 349 ppm in the feed solution was unexpectedly high in comparison with the cobalt flux obtained under the similar conditions with the conventional SLM described in Example 3. The flux for the latter, even at a higher cobalt concentration of 358 in the feed solution, was only 1.954 g/(m²*hr). Thus, the cobalt flux with the present invention was more than 3.5 times higher than that with the conventional SLM. In addition, the extractant concentration of 8 wt. % for the present Example was much lower than that of about 37 wt. % for the conventional SLM in Example 3. As mentioned, a higher extractant concentration should generally give a higher flux. Again, the high flux was an unexpected result of the present invention.

Examples 4–7 also served to investigate the effect of dodecanol concentration on cobalt flux. As shown in Table 8, the effect of dodecanol concentration on cobalt flux in these examples was not very significant for dodecanol concentrations of 2 wt. % and 3 wt. %.

TABLE 8

| Co Results Time (min.) | pH | Cyanex 301 Strip (ppm) | Strip Dispersion Feed (ppm) | Feed Flux (g/(m²*hr)) | 2.5M H₂SO₄ k value (cm/sec) |
|---|---|---|---|---|---|
| 0 | 2.3 | 10173 | 551 | | |
| 5 | | | 349 | 6.926 | 0.000435 |
| 10 | | 14334 | 195 | 5.280 | 0.000554 |
| 15 | | | 95.6 | 3.408 | 0.000679 |
| 20 | | 17505 | 43.2 | 1.683 | 0.000686 |
| 30 | | 18500 | 10.1 | 0.624 | 0.000727 |

Example 8
Orgainc Solution Comprising 8% Extractant and 1% Dodecanol for Cobalt

The experimental procedure for this example was the same as the described in Examples 1, 4, and 6, except that a feed solution containing 576 ppm cobalt and an organic solution of the strip dispersion containing 8 wt. % di(2,4,4-trimethylpentyl)dithiophosphinic acid (e.g., Cyanex 301), 1 wt. % dodecanol, and 91 wt. % Isopar L were used. Samples of the feed and strip solutions were collected at timed intervals and analyzed by ICP as described in the general procedure above. Fluxes and k values were then calculated and are reported in Table 9.

The cobalt was removed from the feed solution, concentrated, and recovered in the aqueous strip solution. The cobalt flux of 6.171 g/(m²*hr) at the cobalt concentration of 396 ppm in the feed solution was unexpectedly high in comparison with the cobalt flux obtained under the similar conditions with the conventional SLM described in Example 3. The flux for the latter at a cobalt concentration of 358 ppm in the feed solution was only 1.954 g/(m²*hr). Thus, the cobalt flux with the present invention was about 3.2 times higher than that with the conventional SLM. In addition, the extractant concentration of 8 wt. % for this example was much lower than that of about 37 wt. % for the conventional SLM in Example 3. As mentioned, a higher extractant concentration should generally give a higher flux. Again, the high flux was an unexpected result of the present invention.

TABLE 9

| Co Results | | Cyanex 301 | Strip Dispersion | | 2.5M $H_2SO_4$ |
|---|---|---|---|---|---|
| Time (min.) | pH | Strip (ppm) | Feed (ppm) | Feed Flux (g/($m^2$*hr)) | k value (cm/sec) |
| 0 | 2.3 | 2526 | 576 | | |
| 5 | | | 396 | 6.171 | 0.000357 |
| 10 | | 4726 | 251 | 4.971 | 0.000434 |
| 15 | | | 146 | 3.600 | 0.000516 |
| 20 | | 7926 | 73.7 | 2.479 | 0.000651 |
| 30 | | 9871 | 16.5 | 0.981 | 0.000713 |

Example 9
Organic Solution Comprising 8% Extractant and 1% Dodecanol for Cobalt

The experimental procedure for this example was the same as that described in Example 8, except that a feed solution containing 570 ppm cobalt and the used strip dispersion from Example 8 were employed. The excess aqueous strip and organic solutions from the strip dispersion samples from Example 8 were returned to the strip dispersion tank before the start of this experiment. Samples of the feed and strip solutions were collected at timed intervals and analyzed by ICP as described in the general procedure above. Fluxes and k values were then calculated and are reported in Table 10.

Tthe cobalt was removed from the feed solution, concentrated, and recovered in the aqueous strip solution. The cobalt flux of 7.269 g/($m^2$*hr) at the cobalt concentration of 358 ppm in the feed solution was unexpectedly high in comparison with the cobalt flux obtained under the similar conditions with the conventional SLM described in Example 3. The flux for the latter, even at the same cobalt concentration of 358 in the feed solution, was only 1.954 g/($m^2$*hr). Thus, the cobalt flux with the present invention was more than 3.7 times higher than that with the conventional SLM. In addition, the extractant concentration of 8 wt. % for the present example was much lower than that of about 37 wt. % for the conventional SLM in Example 3. As mentioned, a higher extractant concentration should generally give a higher flux. Again, the high flux was an unexpected result of the present invention.

Examples 4–9 also served to investigate the effect of the concentration of the modifier, dodecanol, on cobalt flux. As shown from these examples, the effect of dodecanol concentration on cobalt flux was not very significant for dodecanol concentrations ranging from 1 wt. % to 3 wt. %. In other words, dodecanol concentrations ranging from 1 wt. % to 3 wt. % were effective.

TABLE 10

| Co Results | | Cyanex 301 | Strip Dispersion | | 2.5M $H_2SO_4$ |
|---|---|---|---|---|---|
| Time (min.) | pH | Strip (ppm) | Feed (ppm) | Feed Flux (g/($m^2$*hr)) | k value (cm/sec) |
| 0 | 2.3 | 10182 | 570 | | |
| 5 | | | 358 | 7.269 | 0.000443 |
| 10 | | 14060 | 198 | 5.486 | 0.000564 |
| 15 | | | 95.4 | 3.518 | 0.000695 |

TABLE 10-continued

| Co Results | | Cyanex 301 | Strip Dispersion | | 2.5M $H_2SO_4$ |
|---|---|---|---|---|---|
| Time (min.) | pH | Strip (ppm) | Feed (ppm) | Feed Flux (g/($m^2$*hr)) | k value (cm/sec) |
| 20 | | 16971 | 45.2 | 1.721 | 0.000711 |
| 30 | | 17248 | 9.16 | 0.618 | 0.000760 |

Example 10
Cobalt Removed to Low Concentration in Treated Feed and Concentrated to High Concentration in Strip The experimental procedure for this example was the same as that described in Example 1, except that a 1-liter feed solution containing 524 ppm cobalt with pH 2; an 800-ml organic solution of 8 wt. % di(2,4,4-trimethylpentyl) dithiophosphinic acid (e.g., Cyanex 301), 2 wt. % dodecanol; and 90 wt. % Isopar L, and a 60-ml strip solution of 5 M hydrochloric acid were used. The pH of the feed solution was maintained at 2.0±0.1 by adding 5 M NaOH as needed. Samples of the feed and strip solutions were collected at timed intervals and analyzed by ICP as described in the general procedure above. Fluxes and k values were then calculated and are reported in Table 11.

The cobalt concentration of the feed solution was changed from 524 ppm to 0.7 ppm in just 15 minutes where the recycle mode of operation was used for both the feed solution and the strip dispersion. On the other hand, the cobalt was recovered and concentrated to about 30,000 ppm in the aqueous strip solution at the same time.

TABLE 11

| Co Results | | Cyanex 301 | Strip Dispersion | | 5M HCl |
|---|---|---|---|---|---|
| Time (min.) | PH | Strip (ppm) | Feed (ppm) | Feed Flux (g/($m^2$*hr)) | k value (cm/sec) |
| 0 | 2.0 | | 524 | | |
| 2.5 | | | 237 | 4.92 | 0.000378 |
| 5 | | | 99.9 | 2.35 | 0.000411 |
| 10 | | | 6.75 | 0.8 | 0.000642 |
| 15 | | 29,809 | 0.7 | 0.05 | 0.000538 |

Example 11
Cobalt Removed from Feed and Concentrated to Very High Concentration in Strip The experimental procedure for this example was the same as that described in Example 1, except that a 40-liter feed solution containing 492 ppm cobalt with pH 2; a 900-ml organic solution of 8 wt. % di(2,4,4-trimethylpentyl) dithiophosphinic acid (e.g., Cyanex 301), 2 wt. % dodecanol, and 90 wt. % Isopar L; and a 105-ml strip solution of 6.5 M hydrochloric acid were used. The pH of the feed solution was maintained at 2.0±0.1 by adding 5 M NaOH as needed. Samples of the feed and strip solutions were collected at timed intervals and analyzed by ICP as described in the general procedure above. Fluxes and k values were then calculated and are reported in Table 12.

The cobalt was removed from the feed solution, recovered, and concentrated to more than 96,000 ppm in the aqueous strip solution in 6 hours using the recycle mode of operation for both the feed solution and the strip dispersion. The cobalt concentration in the strip solution was more than 195 times the original feed concentration.

TABLE 12

| Co Results | | Cyanex 301 | Strip Dispersion | | 5M HCl |
|---|---|---|---|---|---|
| Time (min.) | pH | Strip (ppm) | Feed (ppm) | Feed Flux (g/(m$^2$*hr)) | k value (cm/sec) |
| 0 | 2.0 | 3,122 | 492 | | |
| 60 | | 32,117 | 376 | 3.31 | 0.000213 |
| 120 | | 56,101 | 286 | 2.57 | 0.000217 |
| 180 | | 76,433 | 220 | 1.89 | 0.000208 |
| 240 | | 87,966 | 163 | 1.63 | 0.000238 |
| 300 | | 91,887 | 137 | 0.74 | 0.000138 |
| 360 | | 96,389 | 129 | 0.23 | 0.000048 |

Example 12
Copper Removed to Low Concentration in Treated Feed and Concentrated to High Concentration in Strip The experimental procedure for this example was the same as that described in Example 1, except that a 5-liter feed solution containing 151 ppm copper and 556 ppm zinc with pH 1.9; a 950-ml organic solution of 15 wt. % nonylsalicyl aldoxime and ketoxine extractant system (e.g., LIX 973N containing about 46% nonylsalicyl aldoxime, 18% ketoxime, 6% nonylphenol, and 30% diluent), 2 wt. % dodecanol, and 83 wt. % n-dodecane; and a 50-ml strip solution of 3 M sulfuric acid were used. The pH of the feed solution was maintained at 1.9±0.1 by adding 5 M NaOH as needed. Samples of the feed and strip solutions were collected at timed intervals and analyzed by ICP as described in the general procedure above. Fluxes and k values were then calculated and are reported in Table 13.

The copper concentration of the feed solution was changed from 151 ppm to 0.07 ppm in just 90 minutes using the recycle mode of operation for both the feed solution and the strip dispersion. On the other hand, the copper was recovered and concentrated to more than 10,000 ppm in the aqueous strip solution in 2 hours. The copper concentration in the strip solution was more than 70 times the original feed concentration.

TABLE 13

| Cu Results | | LIX 973N | Strip Dispersion | | 3M H$_2$SO$_4$ |
|---|---|---|---|---|---|
| Time (min.) | pH | Strip (ppm) | Feed (ppm) | Feed Flux (g/(m$^2$*hr)) | k value (cm/sec) |
| 0 | 1.9 | 4,834 | 151 | | |
| 10 | | | 61.4 | 1.92 | 0.000536 |
| 30 | | | 10.4 | 0.546 | 0.000528 |
| 60 | | | 1.73 | 0.062 | 0.000356 |
| 90 | | | 0.07 | 0.012 | 0.000636 |
| 120 | | 10,708 | 0 | 0.001 | — |

Example 13
Zinc Removed to Low Concentration in Treated Feed and Concentrated to High Concentration in Strip The experimental procedure for this example was the same as that described in Examples 1 and 12, except that the 5-liter feed solution treated in Example 12 containing 556 ppm zinc with pH 1.9; a 850-ml organic solution of 8 wt. % di(2,4,4-trimethylpentyl)dithiophosphinic acid (e.g., Cyanex 301), 2 wt. % dodecanol, and 90 wt. % n-dodecane; and a 150-ml strip solution of 3 M sulfuric acid were used. The pH of the feed solution was maintained at 1.9±0.1 by adding 5 M NaOH as needed. Samples of the feed and strip solutions were collected at timed intervals and analyzed by ICP as described in the general procedure above. Fluxes and k values were then calculated and are reported in Table 14.

The zinc concentration in the feed solution was changed from 556 ppm to 0.275 ppm in just 2 hours using the recycle mode of operation for both the feed solution and the strip dispersion. On the other hand, the zinc was recovered and concentrated to more than 17,000 ppm in the aqueous strip solution at the same time. The zinc concentration in the strip solution was more than 31 times the original feed concentration.

TABLE 14

| Zn Results | | Cyanex 301 | Strip Dispersion | | 3M H$_2$SO$_4$ |
|---|---|---|---|---|---|
| Time (min.) | pH | Strip (ppm) | Feed (ppm) | Feed Flux (g/(m$^2$*hr)) | k value (cm/sec) |
| 0 | 1.9 | 4,644 | 556 | | |
| 10 | | | 405 | 3.24 | 0.000189 |
| 30 | | | 195 | 2.25 | 0.000218 |
| 60 | | | 16.7 | 1.27 | 0.000488 |
| 90 | | | 1.04 | 0.112 | 0.000551 |
| 120 | | 17,713 | 0.275 | 0.005 | 0.000264 |

Example 14
Nickel Removed From Feed and Concentrated to High Concentration in Strip The experimental procedure for this example was the same as that described in Example 1, except that a 2-liter feed solution containing 2,216 ppm nickel with pH 3; a 750-ml organic solution of 24 wt. % of the new extractant, di(2-butyloctyl)monothiophosphoric acid (C12 MTPA), 4 wt. % dodecanol, and 72 wt % n-dodecane; and a 250-ml strip solution of 2.5 M sulfuric acid were used. The pH of the feed solution was maintained at 3±0.1 by adding 5 M NaOH as needed. Samples of the feed and strip solution were collected at timed intervals and analyzed by ICP as described in the general procedure above. Fluxes and k values were then calculated and are reported in Table 15.

The nickel was removed from the feed solution, recovered, and concentrated to more than 10,000 ppm in the aqueous strip solution in 30 minutes in the recycle mode of operation for both the feed solution and the strip dispersion. The nickel concentration in the strip solution was more than 4.8 times the original feed concentration.

TABLE 15

| Ni Results | | C12 MTPA | Strip Dispersion | | 2.5M H$_2$SO$_4$ |
|---|---|---|---|---|---|
| Time (min.) | pH | Strip (ppm) | Feed (ppm) | Feed Flux (g/(m$^2$*hr)) | k value (cm/sec) |
| 0 | 3.0 | 5,836 | 2,216 | | |
| 5 | | | 2,023 | 3.31 | 0.0000434 |
| 10 | | 7,338 | 1,860 | 2.79 | 0.0000400 |
| 20 | | 8,961 | 1,682 | 1.53 | 0.0000240 |
| 30 | | 10,734 | 1,473 | 1.79 | 0.0000316 |

Example 15
Comparative Example Using Conventional D2EHPA for Nickel

The experimental procedure for this example was the similar to that described in Example 14, except that a feed solution containing 2,469 ppm nickel with pH 4.5 and a organic solution containing 24 wt. % of the conventional extractant, di(2-ethylhexyl)phosphoric acid (D2EHPA), were used. The pH of the feed solution was maintained at 4.5±0.1 by adding 5 M NaOH as needed. Samples of the feed and strip solutions were collected at timed intervals and analyzed by ICP as described in the general procedure above. Fluxes and k values were then calculated and are reported in Table 16.

As shown in this table, the nickel fluxes at the nickel concentrations of 2,335 ppm and 1,915 ppm in the feed solution at pH 4.5 were 2.30 and 1.93 g/(m$^2$*hr), respectively. These fluxes were significantly lower than those with the new extractant, C12 MTPA, described in Example 14, i.e., 3.31 and 2.79 g/(m$^2$*hr) at even lower nickel concentrations of 2,023 ppm and 1,860 ppm in the feed solution at an even lower pH of 3, respectively. The flux of a metal increases as the concentration of the metal in the feed solution increases. In view of the feed pH reduction by proton transfer during extraction, an extractant operable at a lower pH can better utilize the length of the module than an extractant operable at a higher pH. Thus, the new extractant, C12 MTPA, outperformed the conventional extractant, D2EHPA, significantly.

TABLE 16

| Ni Results | D2EHPA | Strip Dispersion | | 2.5M H$_2$SO$_4$ |
|---|---|---|---|---|
| Time (min.) | pH | Strip (ppm) | Feed (ppm) | Feed Flux (g/(m$^2$*hr)) | k value (cm/sec) |
| 0 | 4.5 | 1,527 | 2,469 | | |
| 5 | | | 2,335 | 2.30 | 0.0000434 |
| 10 | | | 2,140 | 3.34 | 0.0000400 |
| 20 | | 2,717 | 1,915 | 1.93 | 0.0000240 |
| 30 | | | 1,683 | 1.99 | 0.0000316 |

Example 16

Mercury Removed to Very Low Concentration in Treated Feed and Concentrated in Strip The experimental procedure for this example was the same as that described in Example 1, except that a 2-liter feed solution containing 0.388 ppm mercury with pH 2.5; a 525-ml organic solution of 10 wt. % oleic acid, 10 wt. % dodecanol, and 80 wt. % Isopar L; and a 175-ml strip solution of 3 M nitric acid containing 3 wt. % sodium iodide were used. The pH of the feed solution was maintained at 2.5±0.1 by adding 5 M NaOH as needed. Samples of the feed and strip solutions were collected at timed intervals and analyzed by ICP as described in the general procedure above. Fluxes and k values were then calculated and are reported in Table 17.

The mercury concentration in the feed solution was changed from 0.388 ppm to 0.00084 ppm in just 15 minutes using the recycle mode of operation for both the feed solution and the strip dispersion. The mercury was further reduced to less than 0.00084 ppm in the feed solution, i.e., below the detection limit by ICP spectrometry, in the total run time of just 30 minutes, and it was recovered and concentrated to 21.2 ppm in the aqueous strip solution at the same time. The mercury concentration in the strip solution was more than 54 times the original feed concentration.

TABLE 17

| Hg Results | Oleic Acid | Strip Dispersion | | 3M HNO$_3$ |
|---|---|---|---|---|
| Time (min.) | pH | Strip (ppm) | Feed (ppm) | Feed Flux (g/(m$^2$*hr)) | k value (cm/sec) |
| 0 | 2.5 | ~0 | 0.388 | | |
| 15 | | | 0.00084 | 0.00221 | 0.000973 |
| 30 | | 21.2 | <0.00084 | — | — |

Example 17

Mercury Removed from 3 ppm Feed and Concentrated in Strip

The experimental procedure for this example was the same as that described in Examples 1 and 16, except that a 2-liter feed solution containing 3.01 ppm mercury with pH 2.5; a 525-ml organic solution of 10 wt. % oleic acid, 2.5 wt. % dodecanol, and 87.5 wt. % Isopar L; and a 175-ml strip solution of 3 M nitric acid containing 3 wt. % sodium iodide were used. The pH of the feed solution was maintained at 2.5±0.1 by adding 5 M NaOH as needed. Samples of the feed and strip solutions were collected at timed intervals and analyzed by ICP as described in the general procedure above. Fluxes and k values were then calculated and are reported in Table 18.

As shown in this table, the mercury concentration in the feed solution was changed from 3.01 ppm to 0.0985 ppm in just 20 minutes using the recycle mode of operation for both the feed solution and the strip dispersion. On the other hand, the mercury was recovered and concentrated to 27.4 ppm in the aqueous strip solution at the same time. The mercury concentration in the strip solution was more than 9 times the original feed concentration.

TABLE 18

| Hg Results | Oleic Acid | Strip Dispersion | | 3M HNO$_3$ |
|---|---|---|---|---|
| Time (min.) | pH | Strip (ppm) | Feed (ppm) | Feed Flux (g/(m$^2$*hr)) | k value (cm/sec) |
| 0 | 2.5 | 11.6 | 3.01 | | |
| 5 | | 21.9 | 0.295 | 0.04660 | 0.001107 |
| 10 | | 26.4 | 0.239 | 0.00096 | 0.000100 |
| 15 | | 26.7 | 0.171 | 0.00116 | 0.000159 |
| 20 | | 27.4 | 0.0985 | 0.00124 | 0.000263 |

What is claimed is:

1. A combined supported liquid membrane (SLM)/strip dispersion process for the removal and recovery of one or more metals from a feed solution containing the metals comprising
    (1) treating a feed solution containing one or more metals on one side of an SLM embedded in a microporous support material to remove the metal or metals by the use of a strip dispersion on the other side of the SLM, the strip dispersion being formed by dispersing an aqueous strip solution in an organic liquid comprising an extractant with a mixer; and
    (2) allowing the strip dispersion or a part of the strip dispersion to separate into two phases, an organic liquid phase and an aqueous strip solution phase containing a concentrated metal solution.

2. The process of claim 1 wherein the metal is selected from the group consisting of cobalt, copper, zinc, nickel, mercury, lead, cadmium, silver, europium, lanthanum, neodymium, praseodymium, gadolinium, selenium, and mixtures thereof.

3. The process of claim 2 wherein the metal is selected from the group consisting of cobalt, copper, zinc, nickel, mercury, and mixtures thereof.

4. The process of claim 1 wherein the feed solution is treated at a flux of about 3 g/(m$^2$*hr) or higher.

5. The process of claim 1 wherein the aqueous strip solution of the strip dispersion comprises an acid.

6. The process of claim 5 wherein the acid is selected from the group consisting of sulfuric acid, hydrochloric acid, nitric acid, phosphoric acid, acetic acid, and mixtures thereof.

7. The process of claim 1 wherein the extractant is di(2-butyloctyl)monothiophosphoric acid.

8. The process of claim 1 wherein the organic liquid of the strip dispersion further comprises a modifier in a hydrocarbon solvent or mixture.

9. The process of claim 1 wherein the organic liquid of the strip dispersion comprises about 2 wt. % to about 100 wt. % extractant and about 0 wt. % to about 20 wt. % modifier in a hydrocarbon solvent or mixture.

10. The process of claim 9 wherein the organic liquid of the strip dispersion comprises about 5 wt. % to about 40 wt. % extractant and about 1 wt. % to about 10 wt. % modifier in a hydrocarbon solvent or mixture.

11. The process of claim 8 wherein the modifier is selected from the group consisting of alcohols, nitrophenyl alkyl ethers, trialkyl phosphates, and mixtures thereof.

12. The process of claim 11 wherein the alcohol is selected from the group consisting of hexanol, heptanol, octanol, nonanol, decanol, undecanol, dodecanol, tridecanol, tetradecanol, pentadecanol, hexadecanol, heptadacanol, octadecanol, and mixtures thereof.

13. The process of claim 11 wherein the nitrophenyl alkyl ether is selected from the group consisting of o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether, and mixtures thereof.

14. The process of claim 11 wherein the trialkyl phosphate is selected from the group consisting of tributyl phosphate, tris(2-ethylhexyl)phosphate, and mixtures thereof.

15. The process of claim 8 wherein the hydrocarbon solvent is selected from a group consisting of n-decane; n-undecane; n-dodecane; n-tridecane; n-tetradecane; isodecane; isoundecane; isododecane; isotridecane; isotetradecane; isoparaffinic hydrocarbon solvent having a flash point of 92° C., a boiling point of 254° C., a viscosity of 3 cp at 25° C., and a density of 0.791 g/ml at 15.6° C.; and mixtures thereof.

16. The process of claim 1 wherein the microporous support material is selected from the group consisting of polypropylene, polytetrafluoroethylene, polyethylene, polysulfone, polyethersulfone, polyetheretherketone, polyimide, polyamide, and mixtures thereof.

\* \* \* \* \*